United States Patent [19] [11] Patent Number: 4,882,478
Hayashi et al. [45] Date of Patent: Nov. 21, 1989

[54] PHOTOELECTRIC CONVERSION SENSOR WITH SHIFTED ARCUATE ELEMENTS

[75] Inventors: Shigeru Hayashi; Takasui Saito; Shoji Horiuchi, all of Chofu; Tadashi Takahashi, Tokyo, all of Japan

[73] Assignee: Hideo Nagasu and Tohnichi Computer Applications Co., Ltd., Japan

[21] Appl. No.: 162,906

[22] Filed: Mar. 2, 1988

[30] Foreign Application Priority Data

Mar. 4, 1987 [JP] Japan .................. 62-49776

[51] Int. Cl.$^4$ .................. H01J 40/14; G01N 21/00
[52] U.S. Cl. .................. 250/211 R; 250/209; 356/343
[58] Field of Search .................. 356/343, 338, 340; 250/574, 211 R, 209

[56] References Cited

U.S. PATENT DOCUMENTS 4,037,965 7/1977 Weiss .................. 356/338
4,274,741 6/1981 Cornillault .................. 356/343

FOREIGN PATENT DOCUMENTS 2340252 2/1974 Fed. Rep. of Germany ...... 356/343

Primary Examiner—David C. Nelms
Assistant Examiner—Michael Messinger
Attorney, Agent, or Firm—Scully, Scott, Murphy & Presser

[57] ABSTRACT

A photoelectric conversion sensor for measuring particle size or size distribution based on the light scattering phenomena with excellent precision and higher resolving power. The sensor is characterized in that 8 or more arcuate photoelectric conversion elements each being defined by two concentric arcs with different radii and two adjacent elements in the radial direction are so arranged that the gaps in the radial direction between two adjacent elements in the radial direction can be substantially eliminated by shifting them in the circumferential direction.

2 Claims, 2 Drawing Sheets

PHOTOELECTRIC CONVERSION SENSOR WITH SHIFTED ARCUATE ELEMENTS

BACKGROUND OF THE INVENTION

1. Field of the Invention

The present invention relates to a novel photoelectric conversion sensor used in an apparatus for measuring particle size or size distribution of powder and liquid spray and, more particularly, to a photoelectric conversion sensor used in an apparatus for measuring particle size or size distribution of powder and liquid spray based on the intensity distribution of scattered light obtained by radiating a collimated monochromatic light beam onto a group of particles.

2. Description of the Prior Art

Particles in a collimated monochromatic light beam exhibit scattered intensity patterns corresponding to their diameters. By measuring the scattered intensity pattern generated by a single particle or a group of particles, the particle size or the size distribution of the particles can be determined. The scattered light intensity pattern is symmetrical about the optical axis, and can be detected using a sensor consisting of concentric annular photoelectric conversion elements having their center on the optical axis. The spread of the pattern decreases with the increase of particle size. For this reason, the width of the inner elements should be smaller than the outer elements.

The gaps for insulating adjacent elements in this kind of sensor should be reduced as small as possible from the viewpoints of the precision and the resolving power in particle size measurement. However, in order to improve productivity and to minimize crosstalk between the elements, gaps larger than 10 µm are preferable. Then, near the center, the width of the gaps is comparable with the width of the elements. This situation deteriorates the precision and the resolving power. Furthermore, in order to improve the response of sensors, conductive electrodes made of gold, aluminum or the like must be connected to the inner or outer edge portions or inside the elements. However, such portions do not detect scattered light. Therefore, they are another cause for deterioration of the precision and the resolving power in particle size measurement.

BRIEF SUMMARY OF THE INVENTION

The present invention has been accomplished in order to solve the foregoing problems in the conventional art.

More specifically, it is an object of the present invention to provide a photoelectric conversion sensor for measuring the particle size distribution wherein the radial gaps for insulating adjacent photoelectric conversion elements of the sensor are substantially eliminated to improve the precision and the resolving power in particle size measurement, and the electrodes can be attached to the elements without impairing the function of each photoelectric conversion element.

In a photoelectric conversion sensor for measuring particle size or size distribution with the present invention, 8 or more arcuate photoelectric conversion elements defined by two concentric arcs having different radii and two adjacent elements in the radial direction are so arranged that the gaps in the radial direction between two adjacent elements in the radial direction can be substantially eliminated by shifting them in the circumferential direction.

BRIEF DESCRIPTION OF THE DRAWINGS

These and other objects and features with the present invention will become more apparent from the following description taken in connection with the accompanying drawings, in which.

DESCRIPTION OF PREFERRED EMBODIMENTS

In the first place, the principle of the measurement of particle size distribution will be described briefly.

When a non-polarized, collimated beam with a wavelength $\lambda$ is radiated on isotropic spherical particles having a diameter D, the intensity distribution of light scattered by the spherical particles is determined by the refractive index m and the particle size parameter $\alpha$ ($=\pi D/\lambda$). With the increase of particle size parameter $\alpha$, the amount of scattered light energy in forward small angles with respect to the total amount of scattered light energy is abruptly increased, and the pattern of the angular scattered light intensity distribution in this region is sharply changed with particle size parameter $\alpha$. Based on this characteristic, the particle size of a single particle or the size distribution of a group of particles larger than the wavelength $\lambda$ of the beam can be determined.

Figure 3:
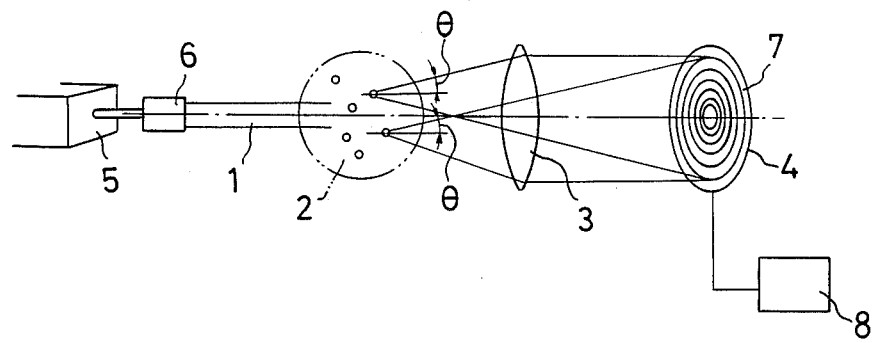
FIG. 3 is a schematic illustration for explaining the principle of the measurement of particle size and its distribution.

As shown in FIG. 3, a laser beam (monochromatic parallel beam) 1 is radiated on a group of particles 2 and scattered light is focused by a receiving lens 3 arranged behind the particle group 2. The components of the light scattered by the particles in the direction of a scattering angle $\theta$ are concentrated to a circular ring with a radius given by the following equation on a focusing surface 4 of the receiving lens regardless of the positiions of the particles and their velocities:

$$r = f \cdot \sin \theta \approx f \cdot \theta$$

The distribution of scattered light intensity $I(\theta)$ on the focusing surface 4 is considered to be the sum of scattered light intensities $I(\theta, \alpha)$ from the individual particles if multiple scattering can be neglected. Assuming that the number particle size distribution is given by $N(\alpha)$, the following relation can be established:

$$\widetilde{I}(\theta) = C_0 \int^\infty I(\theta, \alpha) N(\alpha) d\alpha$$

$I(\theta, \alpha)$ is calculated as a series solution of the scattering equation given by G. Mie. Determination of the particle size distribution from the measurement of $I(\theta)$ is achieved by solving the above integral equation.

More specifically, a laser beam 1 generated by a He-Ne laser tube 5 is expanded through a beam expander or a collimator lens 6 and the resultant collimated beam is radiated on the group of particles 2 to be measured. The scattered laser beams is incident on a receiving lens 3 with, the components in the direction of the scattering angle $\theta$ focused on a circle with radius r on the focusing surface 4 of the receiving lens 3. By disposing an annular photodetector array 7 on the focusing surface 4, the light intensity distribution $I(\theta)$ which is considered the sum of intensities of light scattered by individual particles can be directly measured. The scattered light energy received by each annular photodetector in the array 7 is photoelectrically converted into current signals, which are detected by an optical energy level measurement apparatus 8. The data of the measured current signals are analyzed to give particle size or size distribution.

The photoelectric conversion sensor for measuring particle size distribution with the present invention is obtained by improving the conventional photoelectric conversion sensor used in the above-mentioned measurement method.

Figure 4:
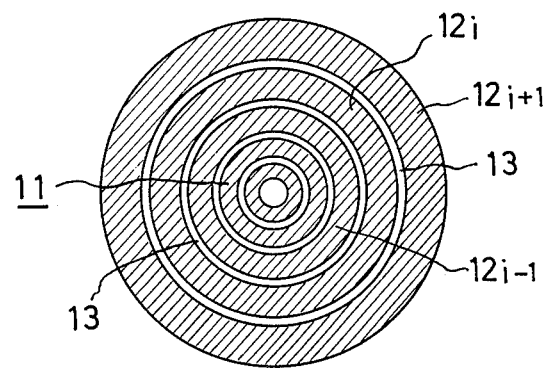
FIG. 4 is a schematic view showing an arrangement of photoelectric conversion elements in a conventional sensor.

FIG. 4 shows a conventional photoelectric conversion sensor. A photoelectric conversion sensor 11 consists of a plurality of concentric annular photoelectric conversion elements 12 having their center on the optical axis.

Gaps 13 for insulating an element $12_i$ of the sensor from an adjacent element $12_{i+1}$ or $12_{i-1}$ are preferably made as small as possible from the viewpoint of the precision and the resolving power in particle size measurement. However, in practice, the design limit is about 10 $\mu$m due to crosstalk between the adjacent elements and productivity. For this reason, with regard to the elements located near the the center, the gaps 13 are too large to be neglected as compared with the width of the elements 12. Therefore, the precision and the resolving power in measurement have been limited. Furthermore, conductive electrodes made of gold, aluminum, or the like must be provided at the edge portions or inside the elements 12. However, these electrodes cannot detect scattered light which also reduces the precision and the resolving power in measurement like in the gaps 13 for insulation.

Figure 1:
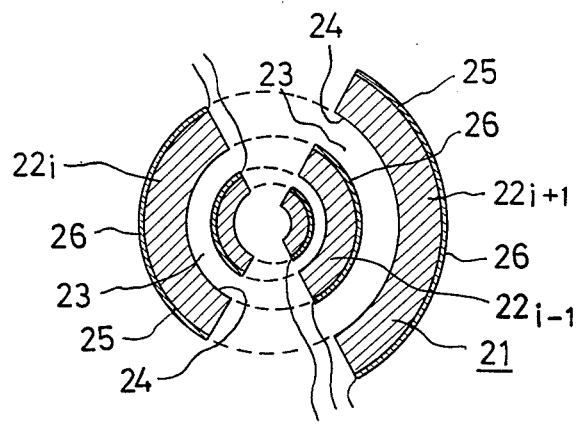
FIG. 1 is a schematic view showing an arrangement of a photoelectric conversion elements in a sensor according to an embodiment of the present invention.

FIG. 1 shows an embodiment of the photoelectric conversion sensor according to the present invention. In the photoelectric conversion sensor 21, each photoelectric conversion element 22 has an arcuate shape. The elements $22_{i-1}$, $22_i$, $22_{i+1}$ . . . are arranged such that they are shifted from one another in the circumferential direction. For example, as shown in FIG. 1, two adjacent elements 22 are shifted by 180° from each other, so that the inner radius of an (i)th element $22_i$ is able to coincide with the outer radius of the (i−1)th element $22_{i-1}$, while the outer radius of the (i)th element $22_i$ is able to coincide with the inner radius of the (i+1)th element $22_{i+1}$. More specifically, since the scattered light intensity pattern is symmetrical about the optical axis, no problem occurs even if each element 22 is not a full ring, but an arcuate shape, thereby substantially eliminating gaps between the adjacent elements.

Since inner and outer edges 24 and 25 of each element face gaps with a sufficient width 23, an electrode 26 can be easily attached along any of these edges without impairing the function of the element 22.

Figure 2:
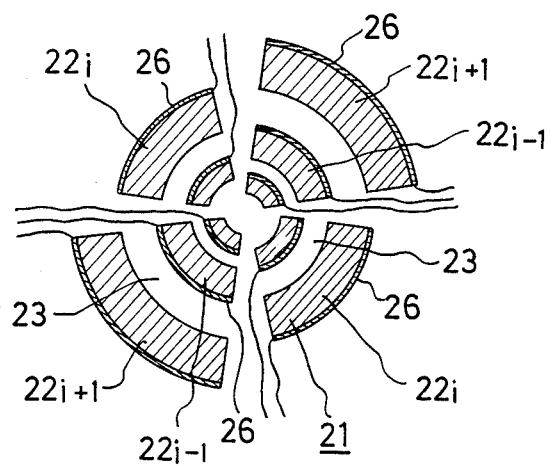
FIG. 2 is a schematic view showing an arrangement according to another embodiment of the present invention.

FIG. 2 shows another embodiment of the present invention. Each element 22 of the sensor 21 shown in FIG. 1 is divided into two pieces, and these pieces are symmetrically arranged to the center. With this arrangement, the effect as described above can be obtained. The present invention is not limited to the illustrated embodiments. The elements can be arranged in various patterns to be shifted from one another according to the principle of the present invention.

As described above, the arcuate photoelectric conversion elements are so arranged that the gaps in the radial direction between two adjacent elements can be substantially eliminated by shifting them in the circumferential direction. Therefore, the precision and the resolving power in measurement can be significantly improved. In addition, since the inner and outer edges of the photoelectric conversion elements face sufficient gaps, electrodes can be easily attached to the elements without impairing their function and crosstalk between the adjacent elements can be minimized.

What is claimed is:

1. A photoelectric conversion sensor wherein 8 or more arcuate photoelectric conversion elements are each defined by two concentric arcs with different radii, with adjacent elements in the radial direction shifted in the circumferential direction so that the gaps in the radial direction between adjacent elements in the radial direction are substantially eliminated and there is no substantial overlap in the radial direction between radially adjacent elements.

2. A photoelectric conversion sensor as in claim 1, wherein adjacent elements in the radial direction are shifted in the circumferential direction by 180° from each other and the inner radius of an (i)th element coincides with the outer radius of the (i−1)th element, while the outer radius of the (i)th element coincides with the inner radius of the (i+1)th element.

* * * * *